US011040117B2

(12) United States Patent
Durham

(10) Patent No.: US 11,040,117 B2
(45) Date of Patent: Jun. 22, 2021

(54) TREATMENT OF A SUBTYPE OF ASD

(71) Applicant: Stalicla S.A., Geneva (CH)

(72) Inventor: Lynn Durham, Geneva (CH)

(73) Assignee: Stalicla S.A., Geneva (CH)

( * ) Notice: Subject to any disclaimer, the term of this patent is extended or adjusted under 35 U.S.C. 154(b) by 0 days.

(21) Appl. No.: 16/182,546

(22) Filed: Nov. 6, 2018

(65) Prior Publication Data

US 2019/0134152 A1 May 9, 2019

Related U.S. Application Data

(60) Provisional application No. 62/582,198, filed on Nov. 6, 2017.

(30) Foreign Application Priority Data

Nov. 6, 2017 (EP) ..................................... 17200185

(51) Int. Cl.
| | | |
|---|---|---|
| *A61K 49/00* | (2006.01) | |
| *A61K 31/26* | (2006.01) | |
| *A61P 25/00* | (2006.01) | |
| *A61K 31/10* | (2006.01) | |
| *A61K 31/155* | (2006.01) | |
| *A61K 31/192* | (2006.01) | |
| *A61K 31/203* | (2006.01) | |
| *A61K 31/343* | (2006.01) | |
| *A61K 31/352* | (2006.01) | |
| *A61K 31/365* | (2006.01) | |
| *A61K 31/375* | (2006.01) | |
| *A61K 31/4409* | (2006.01) | |
| *A61K 31/4425* | (2006.01) | |
| *A61K 36/062* | (2006.01) | |
| *A61K 38/17* | (2006.01) | |
| *A61B 5/16* | (2006.01) | |

(52) U.S. Cl.
CPC .......... *A61K 49/0004* (2013.01); *A61B 5/167* (2013.01); *A61K 31/10* (2013.01); *A61K 31/155* (2013.01); *A61K 31/192* (2013.01); *A61K 31/203* (2013.01); *A61K 31/26* (2013.01); *A61K 31/343* (2013.01); *A61K 31/352* (2013.01); *A61K 31/365* (2013.01); *A61K 31/375* (2013.01); *A61K 31/4409* (2013.01); *A61K 31/4425* (2013.01); *A61K 36/062* (2013.01); *A61K 38/1706* (2013.01); *A61K 38/1709* (2013.01); *A61P 25/00* (2018.01)

(58) Field of Classification Search
None
See application file for complete search history.

(56) References Cited

FOREIGN PATENT DOCUMENTS

WO WO-2010062681 A2 * 6/2010 .............. A61P 25/00
WO WO-2014172490 A1 * 10/2014 ........... C12Q 1/6883

OTHER PUBLICATIONS

Song et al., "Autonomic Dysfunction and Autism: Subtypes and Clinical Perspectives", North American Journal of Medicine and Science, Oct. 2016, pp. 172-180 (Year: 2016).*
Coleta et al., "Assessment of luteolin (3',4',5,6-tetrahydroxyflavone) neuropharmacological activity", Behavioral Brain Research, 2008, pp. 75-82 (Year: 2008).*
Dolske et al. "A Preliminary Trial of Ascorbic Acid as Supplemental Therapy for Autism", Prog. Neuro-Pscychopharmacol. & Biol. Psychiat., 1993, pp. 765-774 (Year: 1993).*
Song et al.,"Autonomic Dysfunction and Autism: Subtypes and Clinical Perspective", North American Journal of Medicine and Science, 2016 (Year: 2016).*
Tang et al. "Luteolin inhibits Nrf2 leading to negative regulation of the Nrf2/ARE pathway and sensitization of human lung carcinoma A549 cells to therapeutic drugs", Free Radical Biology and Medicine, 2011, pp. 1599-1609. (Year: 2011).*
Zhu et al., "An overview of chemical inhibitors of the Nrf2-ARE signaling pathway and their potential applications in cancer therapy", Free Radical Biology and Medicine, 2016, pp. 544-556 (Year: 2016).*
Anagnostou et al. "Metform for Treatment of Overweight Induced by Atypical Antipsychotic Medication in Young People with Austism Spectrum Disorder", JAMA Psychiatry, Aug. 24, 2016, pp. 928-937 (Year: 2016).*
Do et al., "Metformin inhibits heme oxygenase-1 expression in cancer cells through inactivation of Raf-ERK-Nrf2 signaling and AMPK-independent pathways", Toxicology and Applied Pharmacology, 2013, pp. 229-238 (Year: 2013).*
Abrahams, et al., "Advances in autism genetics: on the threshold of a new neurobiology," Nat Rev Genet., vol. 9(6), p. 493 (Jun. 2008).
Bernier et al; Disruptive CHD8 mutations define a subtype of autism early in development; Cell, vol. 158(2), pp. 263-276 (Jul. 2014).
Bochner et al., "Assay of the multiple energy-producing pathways of mammalian cells," PLoS One, 6(3):e18147 (2011).
De Rubeis, et al., "Synaptic, transcriptional and chromatin genes disrupted in autism," Nature., 13; 515 (7526), pp. 209-215 (Nov. 2014).

(Continued)

*Primary Examiner* — Lianko G Garyu
(74) *Attorney, Agent, or Firm* — Millen White Zelano and Branigan, PC

(57) ABSTRACT

The present invention is directed to a pharmaceutical composition comprising an Nrf2-inhibitor. Likewise, the present invention is directed to a pharmaceutical composition for use in the treatment of ASD in a patient, comprising: determining whether the patient suffers from ASD subtype 1 and administering a therapeutically effective amount of an Nrf2-inhibitor if the patients suffers from ASD subtype 1, wherein determining whether the patient suffers from ASD subtype 1 comprises administering the patient an Nrf2-activator and identifying the patient as suffering from ASD subtype 1 if he shows a negative response.

2 Claims, No Drawings

(56) References Cited

OTHER PUBLICATIONS

Dreger et al., "Nrf2-dependent upregulation of antioxidative enzymes: a novel pathway for proteasome inhibitor-mediated cardioprotection.," Cardiovasc Research, 83(2): pp. 354-361 (2009).

Eapen, et al., "Autism Spectrum Disorders: From genotypes to phenotypes," Front Hum Neurosci. 8: p. 914 (2014).

Folstein, et al., "Infantile autism: a genetic study of 21 twin pairs," *J Child Psychol. Psyquiatry*, Sep;18(4): 297-321 (1977).

Gilman, et al., "Rare de novo variants associated with autism implicate a large functional network of genes involved in information and function of synapses," Neuron., vol. 70(5), pp. 898-907 (Jun. 2011).

Higgins et al., "Transcription factor Nrf2 mediates an adaptive response to sulforaphane that protects fibroblasts in vitro against the cytotoxic effects of electrophiles, peroxides and redox-cycling agents," Toxicol Appl Pharmacol, 2009. 237(3): pp. 267-280 (2009).

Estes et al. "Immune mediators in the brain and peripheral tissues in autism spectrum disorder," *Nature Reviews Neuroscience* 16, 469-486 (2015).

O'Roak et al., "Sporadic autism exomes reveal a highly interconnected protein network of de novo mutations," Nature, vol. 4, pp. 485(7397), pp. 246-250 (Apr. 2012).

Persico et al., Searching for ways out of the autism maze: genetic, epigenetic and environmental clues; *Trends Neuroscience*, vol. 29(7):349-358 (Jul. 2006).

Ronemus et al, "The role of the novo mutations in the genetics of autism spectrum disorders," Nat Rev Genet., vol. 15(2), pp. 133-141 (Feb. 2014).

Sandin, et al., "The Heritability of Autism Spectrum Disorder," JAMA, vol. 318(12), pp. 1182-1184 (2017).

Shin et al., "Role of the Nrf2-ARE pathway in liver diseases," Oxid Med Cell Longev, p. 763257 (2013).

Subramanian, "Characterizing Autism Spectrum Disorders by Key Biochemical Pathways," *Frontiers in Neuroscience*, vol. 9, No. 313, pp. 1131-1143 (Sep. 2015).

Tang, et al., "Loss of mTOR-dependent macroautophagy causes autistic-like synaptic pruning deficits," *Neuron*, 83(5), pp. 1131-1143 (2014).

Zoghbi HY, Bear MF; Synaptic dysfunction in neurodevelopmental disorders associated with autism and intellectual disabilities; Cold Spring Harb Perspect Biol. 1;4(3), 22 pgs (Mar. 2012).

* cited by examiner

TREATMENT OF A SUBTYPE OF ASD

CROSS-REFERENCE TO RELATED APPLICATIONS

This application claims priority from U.S. Provisional Patent Application No. 62/582,198, filed Nov. 6, 2017, and European Patent Application No. 17200185.1, filed Nov. 6, 2017. The contents of these applications are incorporated herein by reference in their entirety.

FIELD OF THE INVENTION

The invention relates to a method of treatment for a subtype of idiopathic autism spectrum disorder (ASD), Phenotype 1, which is characterized by specific molecular and/or genetic underlying alterations.

BACKGROUND OF THE INVENTION

Autism spectrum disorder (ASD) are a group of neurodevelopmental disorder frequently characterized by impairments in social interactions, difficulties with language and communication, and the presence of repetitive, perseverative behaviors (Abrahams B S, Geschwind D H; Advances in autism genetics: on the threshold of a new neurobiology; Nat Rev Genet. 2008 June; 9(6):493), (Zoghbi H Y, Bear M F; Synaptic dysfunction in neurodevelopmental disorders associated with autism and intellectual disabilities; Cold Spring Herb Perspect Biol. 2012 Mar. 1; 4(3)). Characteristic symptoms or behavioral traits of ASD typically appear during the first three years of life and remain present throughout life in the vast majority of patients. Intensity of symptoms may vary from patient to patient and may decrease as the patient develops adaptive skills. Environmental factors, developmental or comorbidities such as epilepsy can also result in a worsening of symptoms. According to the fifth edition of the diagnostic and statistical manual of mental disorders (DSM. 5th Edition. Washington, D.C.: American Psychiatric Association; 2013. American Psychiatric Association. Diagnostic and Statistical Manual of Mental Disorders), ASD is characterized by two sets of core impairments: persisting deficits of social communication and interaction; restricted and repetitive behaviors, interests, activities. Compared to the previous edition (DSM-IV-Text Revision) (DSM-1V-TR 4th Edition. Washington, D.C.: American Psychiatric Association; 2000. American Psychiatric Association. Diagnostic and Statistical Manual of Mental Disorders.) DSM-5 introduced significant changes. In the diagnostic criteria, language abilities not employed in social communication have been de-emphasized. Further, the diagnostic subcategories, namely autistic disorder, Asperger disorder, Rett disorder, childhood disintegrative disorder, and pervasive developmental disorder (PDD) not otherwise specified are now encompassed by the diagnostic criteria for autism spectrum disorder. DSM-5 additionally requires to specify where patient fits within three levels of increasing severity of ASD, from (1) ("requiring support") to (2) ("requiring substantial support"), up to (3) ("requiring very substantial support").

Other related behaviorally based definitions for Autism are proposed under various terminologies in other diagnostic manuals and classification system including the WHO-ICD-10 definition of Autistic Disorder (2017/18 ICD-10-CM Diagnosis Code F84.0) (World Health Organization. (1992). The ICD-10 classification of mental and behavioural disorders: clinical descriptions and diagnostic guidelines (Geneva: World Health Organization). While ASD can be defined by symptoms in core areas, there exists significant heterogeneity in genetics, phenotypes, clinical presentation, and associated comorbidities (Persico A M, Bourgeron T; Searching for ways out of the autism maze: genetic, epigenetic and environmental clues; Trends Neurosci. 2006 July; 29(7):349-358). The genetic contribution to the causation/predisposition to autism is considered to be substantial on the basis of high concordance in monozygous twins (Folstein S. Rutter M; Infantile autism: a genetic study of 21 twin pairs; J Child Psychol Psyquiatry;1977 September;18 (4): 297-321.). A recently published reanalysis of data from a previous study on the familial risk for autism spectrum disorder (ASD) further supports these initial findings suggesting that genetics contributes 83% of the risk for ASD. Environmental factors thus seem to play a minor 17% though significant role in the developmental etiology of ASO. (Sandin S, Lichtenstein P, Kuja-Halkola R, Hultman C, Larsson H, Reichenberg A. The Heritability of Autism Spectrum Disorder. JAMA. 2017; 318(12):1182-1184. doi: 10.1001/jama.2017.12141.) However, to further complexify matters genetic and epigenetic factors intertwine with prenatal and lifelong dynamic environmental factors to draw individual patient pathogenesis. There is growing perception among the scientific community that the current behavioral based approaches to diagnostic do not allow for efficient classification of patients in terms of molecular and genetic alterations, but rather serve as a behavioral umbrella term for a large group of neurodevelopmental disorders with different etiologies. Recent developments of new genetic screening methods (e.g., microarray-based, comparative genomic hybridization assay (a-CGH), whole genome or exome sequencing technics . . . ) have permitted to detect hundreds of genetic risk factors, including common and rare genetic variants, which can increase the likelihood of ASD (Ronemus M. et al; The role of the novo mutations in the genetics of autism spectrum disorders; Nat Rev Genet. 2014 February; 15(2): 133-41). Nevertheless, causal genetic factors can only be identified in 15 to 20% of patients who are screened, thus the vast majority ASD patients are still considered idiopathic.

Many autism susceptibility genes are known to have important roles in brain development, with functions ranging from synaptic transmission to RNA processing and neurogenesis (Gilman S R et al; Rare de novo variants associated with autism implicate a large functional network of genes involved in information and function of synapses; Neuron. 2011 Jun. 9;70(5):898-907. O'Roak B J. et al; Sporadic autism exomes reveal a highly interconnected protein network of de novo mutations; Nature. 2012 Apr. 4; 485(7397):246-50. De Rubeis S. et al; Synaptic, transcriptional and chromatin genes disrupted in autism; Nature. 2014 Nov. 13; 515 (7526): 209-15). However, the plethora of genetic targets has highlighted the need for the ASO research community to understand whether genes implicated in ASD may converge on common cellular and developmental processes.

Evidence has recently accumulated to support the theory that the ever-expanding number of ASD susceptibility genes could in fact converge towards a limited number of molecular pathways. This growing assumption offers important translational opportunities as molecular pathways mediating synaptic and circuit formation are also involved in other physiological processes including modulation of the adaptive and innate immune response (Myka L. Estes M L, McAllister A K (2015), Nature Reviews Neuroscience 16, 469-486), cell proliferation, survival and protein synthesis (Subramanian M, Timmerman C K, Schwartz J L, Pham D L and Meffert M K (2015), Front. Neurosci, 9; 313. Tang G. et al. (2014), Neuron. 83, 1131-1143).

Attempts have been previously made to stratify ASD patients into smaller, more homogeneous subgroups by utilizing specific genetic signatures (Bernier et al; Disruptive CHD8 mutations define a subtype of autism early in development; Cell 2014 Jul. 17; 158 (2): 263-276.) or behavioral and clinical endophenotypes (Eapen V. and Clarke R. A.; Autism Spectrum Disorders: From genotypes to phenotypes; Front Hum Neurosci. 2014; 8:914). However, these strategies face difficulty encompassing the genetic and phenotypic heterogeneity of ASD, and may not assist in the identification of specific neurobiological pathways underlying disease.

Assays on a molecular basis might provide a way to classify ASD patients. However, because of the intrinsic complexity of ASD, its heterogeneity and the complex intertwining of genetic and environmental causal factors, specific biomarkers for ASD which could be used to establish such an assay have yet to be identified. Moreover, because of their specifity, such biomarkers cannot encompass large groups of ASD patients. Such assays could however in the short term come to support the characterization of genotypically, phenotypically or treatment response pre-identified subgroups.

There is therefore a need for for specific treatments for individual subgroups of ASD patients.

Objective Problem to be Solved

The problem to be solved is thus the provision of means to efficiently treat a subgroup ASD patients which show a distinct subtype with regard to multiple underlying genetic and/or molecular causes.

SUMMARY OF THE INVENTION

The present invention solves this problem by providing by providing a pharmaceutical composition comprising an Nrf2-inhibitor.

DETAILED DESCRIPTION OF THE INVENTION

In one aspect, the present invention is directed to a pharmaceutical composition comprising an Nrf2-inhibitor, in another aspect of the invention, the pharmaceutical composition is for use in the treatment of ASD or ASD subtype 1 patients. According to the present invention, ASD subtype 1 patients have a negative response to administration of an Nrf2-activator, therefore, ASD subtype 1 patients will show a positive response to and may be treated with an Nrf2-inhibitor.

An Nrf2-inhibitor according to the present invention may be defined as any molecule that inhibits or downregulates Nrf2 or otherwise decreases its activity.

Nrf2-inhibitors include any molecule which negatively regulates the activation of Nrf2, preferably any natural or synthetic molecule that binds to Nrf2 in the cytoplasm, sends Nrf2 to proteasome digestion, and keeps intracellular Nrf2 concentration low; any molecule which deubiquitinates Keap1 and stabilizes the Keap1-Cu13-E3 ligase complex, and/or enhances the E3 ligase activity, which leads to the binding between Keap1 and Nrf2 and consequently degradation of Nrf2 (e.g., Ubiquitin-specific processing protease 15 (USP15)); any molecule which reduces nuclear accumulation of the Nrf2 protein, blocks expression of proteasomal genes (e.g., s5a/psmd4 and alpha-5/psma5) and reduces proteasome activity regulated by Nrf2 (i.e alkaloids, preferably coffee alkaloids, in particular trigonelline); any molecule which has high capacity of capturing ROS and/or keeps low intracellular ROS levels and results in maintenance of low intracellular Nrf2 activity (e.g., water-soluble vitamins, in particular vitamin C (ascorbic acid) or vitamin E); any molecule which inhibits Nrf2 signalling, thus increasing intracellular oxidative stress (e.g., brusatol).

In a preferred embodiment, the Nrf2-inhibitor for use in the treatment of ASD or ASD subtype 1 is selected from the group consisting of Kelch-like ECH-associated protein 1 (cytosolic inhibitor of Nrf2, INRF$_2$, Kelch-like protein 19, KIAA0132, KLHL19), Kelch-like ECH-associated protein 1 zebrafish, Maft protein zebrafish, Keap 1 protein rat, trigonelline (N-methylnicotinate), tamibarotene, all-trans retinoic acid (ATRA), Lutcolin (Lut), Apigenin (APi), Chrysin (Chry), Wogomin (Wog), 4-methoxychalcone, 3',4',5',5,7-Pentamethox- yflavone(PMF), Epigalocatechin 3-gal-late (EGCG), isoniazid (INH); ethionamide (ETH), ascorbic acid (AA), ARE expression modulator (AEM1), brusatol (Bru), cryptoanshinone (CryP), IM3829 (4-(2-cyclohexylethoxy) aniline), metformin (Met), mycotoxin ochratoxin A (Ota), triptolide (TPL) CBR-031-1, CBR-026-7, CBR-168-5, thiuram disulfides and disulfiram.

In another embodiment, the present invention is directed to a method of treatment of ASD or ASD subtype 1, wherein the treatment comprises administration of a therapeutically effective amount of an Nrf2-inhibitor. In one embodiment, the Nrf2-inhibitor may be selected from the group consisting of Kelch-like ECH-associated protein 1 (cytosolic inhibitor of Nrf2, INRF2, Kelch-like protein 19, KIAA0132, KLHL19), Kelch-like ECH-associated protein 1 zebrafish, Maft protein zebrafish, Keap 1 protein rat, trigonelline (N-methylnicotinate), tamibarotene, all-trans retinoic acid (ATRA), Luteolin (Lut), Apigenin (APi), Chrysin (Chry), Wogomin (Wog), 4-methoxychalcone, 3',4',5',5,7-Pentamethox-yflavone(PMF), Epigalocatechin 3-gal-late (EGCG), isoniazid (INH); ethionamide (ETH), ascorbic acid (AA), ARE expression modulator (AEM1), brusatol (Bru), cryptoanshinone (CryP), IM3829 (4-(2- cyclohexylethoxy)aniline), metformin (Met), mycotoxin ochratoxin A (Ota), triptolide (TPL) CBR-031-1, CBR-026-7, CBR-168-5, thiuram disulfides and disulfiram As used herein, the term autism spectrum disorder (ASD) is understood to cover a family of neurodevelopmental disorders characterized by deficits in social communication and interaction and restricted, repetitive patterns of behavior, interests or activities. In the following, the terms "autism spectrum disorder", "autism" and "ASD" are used interchangeably. The term "idiopathic ASD" refers to ASD having a lack of a clear molecular or genetic alteration causing the reported signs and symptoms. The diagnosis of idiopathic ASD is therefore a diagnosis by exclusion, where the main molecular and genetic known causes of autism must be ruled out Herein, the terms "ASD phenotype 1" and "phenotype 1" are used interchangeably. The term "patient" refers to "ASD patient" and is intended to cover not only humans diagnosed as having ASD, but also humans suspected of having ASD, i.e. subjects presenting behavioral characteristics of ASD and displaying clinical signs of ASD but who have not yet received a formal validation of their diagnostic.

The person skilled in the art is well aware of how a patient may be diagnosed with ASD. For example, the skilled person may follow the criteria set up in "American Psychiatric Association; Diagnostic and Statistical Manual of Mental Disorders (DSM-5) Fifth edition" to give a subject a diagnosis of ASD. Likewise, ASD patients may have been diagnosed according to standardized assessments tools including but not limited to DSM IV, ICD-9, ICD-10, DISCO, ADI-R, ADOS, CHAT.

In other cases, patients may have a well-established DSM-IV diagnosis of autistic disorder, Asperger's disorder, or pervasive developmental disorder not otherwise specified (PDD-NOS).

Additionally, the present invention may be useful for subjects displaying clinical signs of ASD, i.e. persistent deficits in social communication and social interaction across multiple contexts as manifested by the following, currently or by history; restricted, repetitive patterns of behavior, interests, or activities, as manifested by at least two of the following, currently or by history; symptoms present in the early development period (but may not become fully manifest until social demands exceed limited capacities, or maybe masked by learned strategies in later life); symptoms cause clinically significant impairment in social, occupational, or other important areas of current functioning; these disturbances are not better explained by intellectual disability (intellectual development disorder) or global development delay.

ASD may occur with or without accompanying intellectual and/or language impairment. It may he associated with a known medical or genetic condition or an environmental factor or other neurodevelopmental, mental or behavioral disorders.

ASD may occur in different severity levels which may be classified according to impairment in social communication and in terms of restricted, repetitive behavior. Importantly, the term ASD phenotype 1 is not associated with a particular severity level of ASD. The present invention may be applied to patients suffering from any severity level of ASD.

ASD phenotype 1 patients can be defined by the following clinical signs and symptoms: having: 1) at least 1 mandatory characteristics: enlarged head size veresus control population characterized by at least one standard deviation above the mean head circumference (HC) at 24 months and/or formal macrocephaly (HC>97% of the general population) and/or cyclical aggravation of core or ancillary autism symptoms potentiated by periods of infectious events, deciduous tooth loss, post-traumatic injury, endogenous and exogenous temperature variation; 2) and at least 2, most preferably at least 3 of the following 20 characteristics: accelerated hair and nail growth versus control population; Increased tendency to present with lighter colors of skin and eyes as compared to individuals of the same ethnicity; Substantially longer eyelashes than control subjects of the same ethnicity; At least 5 non-contiguous areas of hypopigmented skin, particularly presenting on the back of the patient; Signs of edema during periods of infectious events, deciduous tooth loss, post-traumatic injury, or endogenous and exogenous factors modifying body temperature; more specifically, facial edema located in the periorbital and forehead areas; Increased blood levels of gamma-glutamyl transpeptidase (GGT) as compared to typically developing individuals of the same age and ethnicity; Congenital genitourinary malformations and/or functional impairment to initiate urinating; Hypoplasia of the patella; Frequent episodes of diarrhea specifically before the age of 5 years; Frequent episodes of tinnitus; Thinning of the corpus callosum; Positive family history for hematological malignancies in particular but not limited to myeloma and acute promyelocytic leukemia; Positive family history for rheumatoid arthritis, that is at least two affected first-degree relatives in two consecutive generations; Adverse events in response to acetyl-salicylic acid or its derivatives; Iris coloboma, either monolateral or bilateral; Sleep hyperhidrosis particularly in newborns, toddlers and young children (notably increased night sweating during infancy and childhood—often reported by relatives to requires bed linen changes); Increased Th1/Th2 ratio (i.e. elevated levels of Interleukin 1 beta, Interleukin 6, TNF-alpha, Interferon gamma); Congenital accessory or duplicated spleen; Congenital absence of the cisterna chyli; Reported history of mother suffering from viral or bacterial infection during pregnancy and/or biologically confirmed Maternal immune activation during pregnancy.

The person skilled in the art is aware of ways and methods to administer the Nrf2-inhibitor. For example, the Nrf2-inhibitor may be administered orally, nasally or parenteraily. In a preferred embodiment, the Nrf2-inhibitor may be administered orally.

In order to achieve the desired dosage level, the Nrf2-inhibitor may be administered once daily or in several doses per day. In a preferred embodiment, the Nrf2-inhibitor is administered 3 times daily. In another embodiment, the Nrf2-inhibitor is administered 2 times daily. In another embodiment, the Nrf2-inhibitor is administered 1 time per day.

EXAMPLES

Example 1

Materials & Methods

All patientshad previously received a diagnosis of ASD according to DSM-IV or DSM-5 criteria supported by either ADI-R or ADOS-2 scores. No exclusion criteria were considered for age, gender, or ethnicity, although only cases presenting with non-syndromic or isolated ASD were included in the study in order to avoid confounding factors.

Individuals with idiopathic ASD were classified as Phenotype 1 is they showed:
at least 1 mandatory criterion:
  enlarged head size versus control population characterized by at least one standard deviations above the mean head circumference (HC) during the first 24 months of life and/or formal macrocephaly (HC>97% of the general population)
  and/or
  cyclical aggravation of core autism symptoms potentiated by periods of infectious events, deciduous tooth loss, post-traumatic injury, endogenous and exogenous temperature variation
and
at least 2, and most preferably at least 3 out of the following 20 characteristics
  accelerated hair and nail growth versus control population
  increased tendency to present with lighter colors of skin and eyes as compared to individuals of the same ethnicity
  substantially longer eyelashes than control subjects of the same ethnicity
  at least 5 non-contiguous areas of hypopigmented skin, particularly presenting on the back of the patient
  signs of edema during periods of infectious events, deciduous tooth loss, post-traumatic injury, or endogenous and exogenous factors modifying body temperature; more specifically, facial edema located in the periorbital and forehead areas increased blood levels of gamma-glutamyl transpeptidase (GGT) as compared to typically developing individuals of the same age and ethnicity Congenital genitourinary malformations and/or functional impairment to initiate urinating hypoplasia of the patella frequent episodes of diarrhea specifically before the age of 5 years frequent episodes of tinnitus thinning or absence of the corpus callosum positive family history for hematological malignancies in particular but not limited to myeloma and acute promyelocytic leukemia positive family history for rheumatoid arthritis, that is at least two affected first-degree relatives in two consecutive generations adverse events in response to acetyl-salicylic acid or its derivatives iris coloboma, either monolateral or bilateral sleep hyperhidrosis particularly as babies, toddlers and young children (notably increased night sweating during infancy and childhood—often reported by relatives to requires bed linen changes increased Th1/Th2 ratio (i.e. elevated levels of Interleukin 1 beta, Interleukin 6, TNF-alpha, Interferon gamma)

congenital accessory or duplicated spleen congenital absence of the cisterna chyli reported history of mother suffering from viral or bacterial infection during pregnancy and/or biologically confirmed Maternal immune activation during pregnancy Results A cohort of 313 patients with ASD with complete clinical data in the Greenwood Genetic Center (GGC, SC, USA) database was considered in order to select 20 Phenotype 1 and 20 Non-Phenotype 1 samples.

Out of these 313 patients with ASD in the GGC database, 90 (28.8%) had at least two well documented measures of head circumference taken in the first 24 months of life by a trained physician. Among these 90 patients, 47 (52.2%) matched with at least 1 primary criterion (i.e. head circumference).

The families of the 47 patients with at HC>75 were contacted by telephone to inquire about the presence of the second mandatory criteria for ASD Phenotype 1. The GGC failed to establish contact with the families of 5 of the 47 patients (10.6%). Of the remaining 42 patients from which it was possible to collect further clinical information, 21 (50%) satisfied the ASD Phenotype criteria. Overall, with the exclusion of the 5 cases which could not be followed-up, 21 out of 85 patients (24.7%) fit the criteria for ASD phenotype 1and showed between 3 and 8 of the secondary characteristics.

Example 2

Materials & Methods

Fifteen of the 21 ASD phenotype 1 patients identified in example I were considered for in-vitro analysis. Twenty ASD patients were selected as non-phenotype 1 if they did not match the criteria cited in example 1. Twenty controls were identified as individuals in which no signs or symptoms of neurobehavioral disorders have been detected and were therefore considered as typically developing individuals (TDs).

The phenotype 1 cohort (Ph1) selected for in vitro experiments was composed by 14 males and 1 female (ratio 14:1), with an age range of 2-17 years (average 7.7). For comparison, the non-phenotype 1 (non-ph1) cohort was composed by 19 males and 1 female (ratio 19:1), with an age range of 2-20 years (average 5.25), while the TD cohort was composed by 15 males and 5 females (3:1 ratio) with the age at the time of sample collection ranging from 3 to 8 years (average 5.1)

From all subjects, blood samples were collected and lymphoblastoid cell lines generated. Briefly, tubes containing anticoagulant citrate dextrose (ACD) were used to collect blood samples via venipuncture, in order to ensure that the blood cells remained metabolically active. The tubes were kept at room temperature and processed within 24 hours.

Cell lines were obtained by immortalization of lymphocytes from blood samples using Epstein-Barr virus. The lymphoblastoid cell lines were harvested in Sigma RPMI-1640 with 75 mL fetal bovine serum from Atlanta Biological (Lawrenceville, Ga., USA) and 5 mL L-Glutamine and 5 mL antibiotic/antimycotic from Sigma-Aldrich (St. Louis, Mo., USA).

Energy production of cells was measured using commercially available Phenotype Mammalian MicroArrays (PM-Ms, Biolog, Hayward, Calif., USA).

The compound in each well was designed to be used by the cells, either as the sole energy source or as the metabolic effector influencing the utilization of an energy source ($\alpha$-D-glucose) added in the cell suspension. The production of NADH per well was monitored using a colorimetric redox dye chemistry (Bochner et al. Assay of the multiple energy-producing pathways of mammalian cells. PLoS One 2011, 6(3):e18147). Before plating, cell viability and number were assessed utilizing a BioRad cell counter and a trypan blue dye. The concentration of live cells required for plating was $4\times10^5$ cells/mL, corresponding to 20,000 cells per well in a volume of 50 µL. Only cell lines with viability of 55% or above were utilized for the experiments and, in order to minimize artifacts and biases due to prolonged cell culturing of transformed cells, LCLs were not utilized if they had reached 15 passages. Cells were incubated for 48 h at 37° C. in 5% $CO_2$, using the modified Biolog IF-M1 medium.

The Biolog IF-M1 medium was modified for plates PM-M1 to M4 by adding the following to 100 mL of Biolog IF-M1: 1.1 mL of 100× penicillin/streptomycin solution, 0.16 mL of 200 mM glutamine (final concentration 0.3 mM), and 5.3 mL of Fetal Bovine Serum (FBS, final concentration 5%). For plates PM-M5 to M8, 5.5 mM $\alpha$-D-glucose will be added in place of FBS.

During the 48-hour incubation, the only energy source the cells had was the chemical in the well. After this first incubation, Biolog Redox Dye Mix MB was added (10 µL/well) and the plates were incubated under the same conditions for an additional 24 hours. As the cells metabolized the energy source, tetrazolium dye in the media was reduced, producing a purple color according to the amount of NADH generated.

For the last 24 hours of the experiment, the plates were incubated in the Omnilog system, which collects optical density readings every 15 minutes, generating 96 data-points for each well. The system also elaborated the kinetic curve for the metabolic reaction in each well and extrapolated parameters such as slope, highest point, endpoint, area under the curve (AUC), and lag.

At the end of the 24-hour incubation, the plates were analyzed utilizing a microplate reader with readings at 590 and 750 nm. The first value ($A_{590}$) indicated the highest absorbance peak of the redox dye and the second value ($A_{750}$) gave a measure of the background noise. The relative absorbance ($A_{590-750}$) was calculated per well.

Results

The metabolic findings in Phenotype 1 cells showed a distinctive profile and the molecular abnormalities detected in these samples was consistent with activation of Nrf2 and Nrf2 signaling pathway expected in ASD phenotype 1 and ultimately with the expected abnormalities in phenotype 1.

Clear evidence of increased anti-oxidant activity in phenotype 1 cells is provided in Table 1: whenever the cells were exposed to metabolic effectors promoting high energy production (Area Under the Curve, AUC, on the Y axis of the graphics), non-phenotype 1 and control cells generated high NADH levels, while phenotype 1 cells kept a steady profile in the low range of NADH production.

In order to generate more energy than the baseline levels, human cells need to increase the rate of aerobic metabolism, that occurs mostly in mitochondria and is based on oxidative reactions, which often produce reactive oxygen species (ROS) as by-products. The cellular anti-oxidant activity is increased in phenotype 1 cells because of the constitutive activated Nrf2 signaling pathway, Nrf2 activates a battery of antioxidant and detoxifying genes, such as GST (glutathione-S-transferase), NQO1 (NAD(P)H:quinone oxidoreductase 1), HO-1 (heme oxygenase 1), GCS ((glutamate-cysteine ligase catalytic subunit), and of genes encoding free radical scavengers, such as superoxide dismutase 1 (SOD1) and catalase (Dreger et al., Nrf2-dependent upregulation of antioxidative enzymes: a novel pathway for proteasome inhibitor-mediated cardioprotection. Cardiovasc Res, 2009. 83(2); p, 354-61; Higgins et al., Transcription factor Nrf2 mediates an adaptive response to sulforaphane that protects fibroblasts in vitro against the cytotoxic effects of electrophiles, peroxides and redox-cycling agents. Toxicol Appl Pharmacol, 2009. 237(3): p. 267-80; Shin et al. Role of the Nrf2-ARE pathway in liver diseases. Axid Med Cell Longev, 2013, 2013: p. 763257). Thus, the main impact of the Nrf2 antioxidant activity is on ROS and mitochondrial aerobic metabolism. Nrf2 promotes the inhibition of oxidative reactions, resulting in a decreased energy production by mitochondrial aerobic metabolism, which is reflected in the lower levels of NADH generated by phenotype 1 observed in our metabolic assays.

The PI3K-AKT-mTOR pathway is modulated by the Nrf2 signaling pathway. Area under the curve values (AUC) and endpoint absorbance values (Table 1) show a significantly reduced production of NADH in ASD phenotype 1 cells compared to TDs and non-phenotype 1 cells, when cells were exposed to FGF-1 or hGH, two growth factors that selectively target the PI3K-Akt-mTOR by binding the receptor tyrosine kinase (TRK) expressed in the lymphoblast's membrane. Conversely, no significant differences were detected when the cells were exposed to growth factors that target less specifically the PI3K-AKT-mTOR pathway in LCLs, like insulin-like growth factor 1 (IGF-I) and platelet-derived growth factor AB (PDGF-AB).

Nrf2 exerts a stimulatory effect on NF-κB, inducing a pro-inflammatory profile by enhancing the production of Th1 cytokines. Phenotype 1 cells generate significantly lower levels of NADH than other cells when exposed to Th1 cytokines, such as IL-1β and IL-6, than when exposed to Th2 cytokines, like IL-2 and IL-8. A similar trend was noted in the PM-M8 plate when the cells were exposed to the Th1 cytokines IFN-γ and TNF-α.

All in one those results demonstrate a metabolic profile specific of the ASD phenotype 1 when compared to the ASD non-phenotype 1 patients. This metabolic fingerprint validates the existence of a specific ASD phenotype 1.

TABLE 1

List of some of the wells showing different NADH levels between Phenotype 1 and control samples.

| | substrate | UT Phenotype 1 Patient Average | UT Control Average | P value | Note |
|---|---|---|---|---|---|
| A01 | NegativeControl | 1.2826 | 1.5439 | 0.0210 | UT Control average is higher |
| A02 | NegativeControl | 2.1039 | 2.4861 | 0.0360 | UT Control average is higher |
| A05 | Dextrin | 4.4644 | 6.9303 | 0.0007 | UT Control average is higher |
| A08 | Maltotriose | 4.1511 | 2.9542 | 0.0392 | UT Phenotype Patient average is higher |
| A09 | Maltose | 5.6163 | 3.2355 | 0.0024 | UT Phenotype Patient average is higher |
| A10 | D-Trehalose | 2.6570 | 1.9067 | 0.0277 | UT Phenotype Patient average is higher |
| B01 | D-Glucose-6-Phosphate | 2.1269 | 2.8665 | 0.0085 | UT Control average is higher |
| B02 | D-Glucose-1-Phosphate | 3.7488 | 5.5805 | 0.0002 | UT Control average is higher |
| B04 | D-(+)-Glucose | 11.0869 | 13.7383 | 0.0016 | UT Control average is higher |
| B05 | D-(+)-Glucose | 5.3267 | 6.6308 | 0.0027 | UT Control average is higher |
| B10 | Salicin | 3.1458 | 2.1487 | 0.0157 | UT Phenotype Patient average is higher |
| B12 | N-Acetyl-D-Glucosamine | 1.9120 | 1.4505 | 0.0427 | UT Phenotype Patient average is higher |
| C05 | D-Mannose | 5.5082 | 7.2586 | 0.0003 | UT Control average is higher |
| C10 | Sucrose | 1.4825 | 1.1139 | 0.0302 | UT Phenotype Patient average is higher |
| C12 | Turanose | 2.3111 | 1.6814 | 0.0210 | UT Phenotype Patient average is higher |
| D01 | D-Tagatose | 0.7848 | 0.9824 | 0.0210 | UT Control average is higher |
| D06 | D-Fructose-6-Phosphate | 1.9697 | 2.8775 | 0.0000 | UT Control average is higher |
| E01 | MelibionicAcid | 1.4852 | 1.9700 | 0.0007 | UT Control average is higher |
| E03 | D-Galactose | 2.8088 | 3.7983 | 0.0030 | UT Control average is higher |
| E07 | Pectin | 3.1739 | 2.3056 | 0.0105 | UT Phenotype Patient average is higher |
| E09 | Thymidine | 0.9345 | 0.8003 | 0.0253 | UT Phenotype Patient average is higher |
| E10 | Uridine | 1.7966 | 1.3593 | 0.0230 | UT Phenotype Patient average is higher |
| E11 | Adenosine | 2.7165 | 1.8644 | 0.0068 | UT Phenotype Patient average is higher |

TABLE 1-continued

List of some of the wells showing different NADH levels between Phenotype 1 and control samples.

| | substrate | UT Phenotype 1 Patient Average | UT Control Average | P value | Note |
|---|---|---|---|---|---|
| E12 | Inosine | 5.0562 | 3.3001 | 0.0044 | UT Phenotype Patient average is higher |
| H01 | AcetoaceticAcid | 1.2179 | 1.4480 | 0.0230 | UT Control average is higher |
| H03 | a-Keto-ButyricAcid | 0.9645 | 1.2604 | 0.0076 | UT Control average is higher |
| H10 | PropionicAcid | 1.1854 | 0.7299 | 0.0003 | UT Phenotype Patient average is higher |
| H11 | AceticAcid | 1.5351 | 1.2154 | 0.0210 | UT Phenotype Patient average is higher |
| H12 | HexanoicAcid | 1.3682 | 1.1210 | 0.0463 | UT Phenotype Patient average is higher |
| A05 | NegativeControl | 5.3075 | 6.4793 | 0.0277 | UT Control average is higher |
| B01 | Resistin | 4.5123 | 5.6797 | 0.0129 | UT Control average is higher |
| B05 | Resistin | 3.6909 | 4.6657 | 0.0129 | UT Control average is higher |
| C03 | Ghrelin | 4.2361 | 5.0063 | 0.0392 | UT Control average is higher |
| C05 | Ghrelin | 4.7857 | 6.2623 | 0.0061 | UT Control average is higher |
| C06 | Ghrelin | 5.7492 | 7.2315 | 0.0143 | UT Control average is higher |
| D01 | Gastrin | 4.6075 | 5.8109 | 0.0129 | UT Control average is higher |
| D02 | Gastrin | 3.6864 | 4.5578 | 0.0210 | UT Control average is higher |
| D03 | Gastrin | 4.7024 | 5.9872 | 0.0253 | UT Control average is higher |
| D04 | Gastrin | 4.6552 | 5.9454 | 0.0173 | UT Control average is higher |
| D05 | Gastrin | 3.3230 | 4.3135 | 0.0068 | UT Control average is higher |
| E01 | hGH(Somatotropin) | 3.5131 | 4.2845 | 0.0302 | UT Control average is higher |
| E02 | hGH(Somatotropin) | 6.1886 | 7.6730 | 0.0302 | UT Control average is higher |
| E03 | hGH(Somatotropin) | 5.3069 | 7.0433 | 0.0024 | UT Control average is higher |
| E04 | hGH(Somatotropin) | 4.9185 | 6.0531 | 0.0643 | UT Control average is higher |
| E05 | hGH(Somatotropin) | 3.0475 | 3.7897 | 0.0463 | UT Control average is higher |
| E06 | hGH(Somatotropin) | 3.3055 | 4.3524 | 0.0030 | UT Control average is higher |
| E07 | IGF-I | 4.1864 | 4.7777 | 0.1394 | UT Control average is higher |
| E08 | IGF-I | 6.0383 | 6.4857 | 0.3819 | UT Control average is higher |
| E09 | IGF-I | 5.0086 | 5.1495 | 0.6808 | UT Control average is higher |
| E10 | IGF-I | 5.7454 | 5.8106 | 0.8051 | UT Control average is higher |
| E11 | IGF-I | 4.1026 | 4.2450 | 0.7051 | UT Control average is higher |
| E12 | IGF-I | 3.8620 | 3.8312 | 0.9607 | UT Phenotype Patient average is higher |
| F01 | FGF-1(aFGF) | 4.6635 | 5.4833 | 0.0191 | UT Control average is higher |
| F02 | FGF-1(aFGF) | 6.4952 | 7.7893 | 0.0545 | UT Control average is higher |
| F03 | FGF-1(aFGF) | 6.7217 | 8.0864 | 0.0463 | UT Control average is higher |
| F04 | FGF-1(aFGF) | 4.6164 | 5.5960 | 0.0392 | UT Control average is higher |
| F05 | FGF-1(aFGF) | 6.2132 | 7.6145 | 0.0689 | UT Control average is higher |
| F06 | FGF-1(aFGF) | 6.2023 | 7.3791 | 0.0926 | UT Control average is higher |
| F07 | PDGF-AB | 3.4671 | 4.1317 | 0.0392 | UT Control average is higher |
| F08 | PDGF-AB | 5.7351 | 6.6622 | 0.1066 | UT Control average is higher |
| F09 | PDGF-AB | 6.4721 | 7.0717 | 0.3136 | UT Control average is higher |
| F10 | PDGF-AB | 4.7311 | 4.8924 | 0.7051 | UT Control average is higher |
| F11 | PDGF-AB | 5.2203 | 5.4621 | 0.5644 | UT Control average is higher |
| F12 | PDGF-AB | 4.2885 | 4.5090 | 0.6568 | UT Control average is higher |
| G01 | IL-1 beta | 3.7944 | 4.6514 | 0.0068 | UT Control average is higher |
| G02 | IL-1beta | 5.7966 | 6.7024 | 0.1905 | UT Control average is higher |
| G03 | IL-1beta | 6.0344 | 7.2291 | 0.1585 | UT Control average is higher |
| G04 | IL-1beta | 5.6973 | 8.8322 | 0.0800 | UT Control average is higher |
| G05 | IL-1beta | 6.4106 | 7.7595 | 0.0926 | UT Control average is higher |
| G06 | IL-1beta | 4.4971 | 5.3874 | 0.1142 | UT Control average is higher |
| G07 | IL-2 | 5.6683 | 6.3875 | 0.1687 | UT Control average is higher |
| G08 | IL-2 | 3.7132 | 4.2621 | 0.1585 | UT Control average is higher |
| G09 | IL-2 | 4.6178 | 5.1066 | 0.2538 | UT Control average is higher |
| G10 | IL-2 | 5.8067 | 6.5109 | 0.1585 | UT Control average is higher |
| G11 | IL-2 | 4.0105 | 4.4238 | 0.1394 | UT Control average is higher |
| G12 | IL-2 | 4.6692 | 4.6766 | 0.8823 | UT Control average is higher |
| H01 | IL-6 | 4.4499 | 5.0238 | 0.1687 | UT Control average is higher |
| H02 | IL-6 | 3.4820 | 4.0160 | 0.1142 | UT Control average is higher |
| H03 | IL-6 | 4.3322 | 5.1575 | 0.1222 | UT Control average is higher |
| H04 | IL-6 | 4.3861 | 5.1877 | 0.1487 | UT Control average is higher |
| H05 | IL-6 | 4.3835 | 5.0178 | 0.3467 | UT Control average is higher |
| H06 | IL-6 | 4.7685 | 5.6056 | 0.1487 | UT Control average is higher |
| H07 | IL-8 | 5.0911 | 5.7886 | 0.2538 | UT Control average is higher |
| H08 | IL-8 | 3.6180 | 4.2129 | 0.0994 | UT Control average is higher |
| H09 | IL-8 | 3.6674 | 3.9547 | 0.3770 | UT Control average is higher |
| H10 | IL-8 | 3.3435 | 3.7976 | 0.1585 | UT Control average is higher |
| H11 | IL-8 | 3.4478 | 3.6975 | 0.4582 | UT Control average is higher |
| H12 | IL-8 | 4.6088 | 4.7185 | 0.6808 | UT Control average is higher |
| G01 | IFN-gamma | 4.0356 | 4.9801 | 0.0173 | UT Control average is higher |
| G02 | IFN-gamma | 4.7917 | 5.4039 | 0.2270 | UT Control average is higher |
| G03 | IFN-gamma | 4.8744 | 5.8787 | 0.1066 | UT Control average is higher |
| G04 | IFN-gamma | 3.5975 | 4.4725 | 0.0253 | UT Control average is higher |
| G05 | IFN-gamma | 5.4186 | 6.3358 | 0.2680 | UT Control average is higher |
| G06 | IFN-gamma | 4.4249 | 5.2327 | 0.1066 | UT Control average is higher |
| G07 | TNF-alpha | 4.9584 | 5.5748 | 0.3136 | UT Control average is higher |
| G08 | TNF-alpha | 5.0666 | 6.0854 | 0.0743 | UT Control average is higher |
| G09 | TNF-alpha | 4.1134 | 4.7635 | 0.1687 | UT Control average is higher |

TABLE 1-continued

List of some of the wells showing different NADH levels between Phenotype 1 and control samples.

|  | substrate | UT Phenotype 1 Patient Average | UT Control Average | P value | Note |
|---|---|---|---|---|---|
| G10 | TNF-alpha | 4.8733 | 5.5308 | 0.2979 | UT Control average is higher |
| G11 | TNF-alpha | 3.8775 | 4.2126 | 0.4785 | UT Control average is higher |
| G12 | TNF-alpha | 4.3117 | 4.3135 | 0.8307 | UT Control average is higher |

Example 3

Individuals with idiopathic ASD were classified as phenotype 1 is they showed:
at least 1 mandatory characteristics:
  enlarged head size versus control population characterized by at least one standard deviations above the mean head circumference (HC) during the first 24 months of life and/or formal macrocephaly (HC>97% of the general population)
and/or
  cyclical aggravation of core autism symptoms potentiated by periods of infectious events, deciduous tooth lass, post-traumatic injury, endogenous and exogenous temperature variation
and
at least 2, and most preferably at least 3 of the following 20 characteristics:
  accelerated hair and nail growth versus control population
  increased tendency to present with lighter colors of skin and eyes as compared to individuals of the same ethnicity
  substantially longer eyelashes than control subjects of the same ethnicity
  at least 5 non-contiguous areas of hypopigmented skin, particularly presenting on the back of the patient
  signs of edema during periods of infectious events, deciduous tooth loss, post-traumatic injury, or endogenous and exogenous factors modifying body temperature; more specifically, facial edema located in the periorbital and forehead areas
  increased blood levels of gamma-glutamyl transpeptidase (GGT) as compared to typically developing individuals of the same age and ethnicity
  congenital genitourinary malformations and/or functional impairment to initiate urinating
  hypoplasia of the patella
  frequent episodes of diarrhea specifically before the age of 5 years
  frequent episodes of tinnitus
  thinning or absence of the corpus callosum
  positive family history for hematological malignancies in particular but not limited to myeloma and acute promyelocytic leukemia
  positive family history for rheumatoid arthritis, that is at least two affected first-degree relatives in two consecutive generations
  adverse events in response to acetyl-salicylic acid or its derivatives
  iris coloboma, either monolateral or bilateral
  sleep hyperhidrosis particularly as babies, toddlers and young children (notably increased night sweating during infancy and childhood—often reported by relatives to requires bed linen changes
  increased Th1/Th2 ratio (i.e. elevated levels of Interleukin 1 beta, Interleukin 6, TNF-alpha, Interferon gamma)
  congenital accessory or duplicated spleen
  congenital absence of the cisterna chyli
  reported history of mother suffering from viral or bacterial infection during pregnancy and/or biologically confirmed Maternal immune activation during pregnancy The effects of sulforaphane containing Broccoli sprout extract was observed and quantified in 5 individuals suffering from ASD and previously classified as phenotype 1 patients.

Procedure

We describe a procedure consisting of an evaluation of patients with ASD prior and after administration of broccoli sprout extract. The extract was prepared from selected broccoli seeds known to have high yield of sulforaphane which were surface-disinfected and grown (sprouted) for 3 days in a commercial sprouting facility under controlled light and moisture conditions. A boiling water extract was prepared, filtered, cooled, and treated with the enzyme myrosinase (from daikon sprouts) to convert precursor glucosinolates to isothiocyanates. Behavioral evaluation of patients was performed prior, during and after administration of sulforaphane-containing broccoli sprout extract. Baseline evaluation of patients was performed using standard clinical endpoints (ADI-R subscales ADI-SI, ADI-C and ADI-RI).

Challenge regimen consisted of the administration of a Broccoli Sprout Extract dose corresponding to a total daily dosage of 4 µmol/kg of sulforaphane, administered in 3 doses over the course of the day.

TABLE 2

Calculation used to determine which quantity of fresh broccoli sprouts should be used to reach a sulforaphane dosage of 4 µmol/kg in patients administered dry broccoli extract

| Patient # | Weight of ASD patient (kg) | Sulforaphane daily dose (µmol/kg) | Total daily sulforaphane dose (µmol) | Estimated quantity of dry broccoli extract needed (g) | Actual quantity of fresh 3-day old broccoli sprouts used (g) |
|---|---|---|---|---|---|
| Patient 1 | 50 | 4 | 200 | 9.6-17.8 | 150 |
| Patient 2 | 55 | 4 | 220 | 10.5-19.6 | 150 |
| Patient 3 | 22 | 4 | 88 | 4.2-7.8 | 50 |
| Patient 4 | 65 | 4 | 260 | 12.5-23.1 | 175 |
| Patient 5 | 25 | 4 | 100 | 4.8-8.9 | 50 |
| Patient 6 | 32 | 4 | 128 | 6.1-11.4 | 75 |
| Patient 7 | 37 | 4 | 148 | 7.1-13.2 | 100 |

Steps of the calculation:
Estimated sulforaphane content in 50 grams of dry broccoli extract: 102 to 186 mg
Resulting quantity of dry broccoli extract to get 1 mg of sulforaphane: 270 to 500 mg Molecular weight of sulforaphane: 177,29 g/mol Number of moles per milligram of sulforaphane: 5.64 µmol Estimated quantity of dry broccoli extract to get 1 µmol of sulforaphane: 48 to 89 mg Relative weight of dry broccoli extract to fresh 3-day old broccoli sprouts: 10% (90% is water)

Estimated quantity of fresh 3-day old broccoli sprouts to get 1 µmol of sulforaphane: 480 to 890 mg The assessment of baseline scores and post challenge test scores was conducted by two experienced clinicians with extensive experience in conducting ASD clinical assessments, both of which separately rated the patients. In case of diverging scores in test subscales at baseline or after administration of the challenge test, the lowest severity score was retained. Assessment of clinical endpoints was performed at day 3 of administration of challenge test. Behavioral Outcome Measures: (primary efficacy endpoints): ABC, SRS; CGI-S, CGI-I and ADI-R (ADI-SI, ADI-C, ADI-RI).

In order to confirm phenotype 1 patient, at least one of the following primary outcomes had to be attained after challenging the patient by with sulforaphane administration:

ADI-R: at least 10% increase in ADI-R scores, preferably but not limit to the following subscales: ADI-SI, ADI-C.

CGI-I: patient rated as much worse or very much worse.

Results

Demographics: Five male patients, diagnosed by experienced clinical psychiatrist using strict DSM-5 criteria for Autism Spectrum Disorder. Patient 5 had a history of neurological disease and was treated with Lithium (concomitant medication).

All patients were classified as suffering from a non-syndromic type of autism spectrum disorder. None of them was reported to carry any known autistic linked single gene disorder or copy number variation (CNV) or any other structural variants Four patients used functional language, whereas the remaining one did not (Patient 2). Thus, that last subject was solely administered B1 and B4 module of the "Qualitative abnormalities in Communication" domain.

All patients matched the ASD phenotype 1 criteria.

Scores for the ADI-R in all subdomains were above the autism cut off (ADI-R-SI cut off=10, ADI-R C Verbal cut off=8, Nonverbal cut off=7; ADI-R-RI cut off=3) in all subjects validating preexisting clinical diagnosis of ASD. ADI-R baseline evaluations were conducted prior to any change or adjunct in intervention (either pharmaceutical and/or behavioral).

TABLE 3

ASD diagnostic scores prior to challenge test, cut off for ASD specified in brackets).

| Patient | ADI-R-SI | ARI-R-C | ADI-R-RI |
|---|---|---|---|
| Patent 1 | 20 (10) | 10 (7) | 3 (3) |
| Patient 2 | 25 (10) | 12 (8) | 5 (3) |
| Patient 3 | 18 (10) | 15 (8) | 3 (3) |
| Patient 4 | 20 (10) | 14 (8) | 3 (3) |
| Patient 5 | 16 (10) | 12 (8) | 3 (3) |

Summary of the standardized scores showing the effect of Broccoli Sprout Extract (sulforaphane) administration in all five patients:

TABLE 4

ASD scores comparison prior and during challenge test.

| Standardized test | Patient 1 B score | Patient 1 S score | Change (%) |
|---|---|---|---|
| ADI-R-SI | 20 | 24 | 20 |
| ADI-R-C | 10 | 12 | 20 |
| ADI-R-RI | 3 | 4 | 33 |
| Standardized test | Patient 2 B score | Patient 2 S score | Change (%) |
| ADI-R-SI | 25 | 28 | 11 |
| ADI-R-C | 12 | 16 | 33 |
| ADI-R-RI | 5 | 7 | 40 |
| Standardized test | Patient 4 B score | Patient 4 S score | Change (%) |
| ADI-R-SI | 20 | 24 | 20 |
| ADI-R-C | 14 | 19 | 36 |
| ADI-R-RI | 3 | 4 | 33 |
| Standardized test | Patient 5 B score | Patient 3 S score | Change (%) |
| ADI-R-SI | 16 | 21 | 31 |
| ADI-R-C | 12 | 17 | 42 |
| ADI-R-RI | 3 | 4 | 33 |

Note:
B score = Baseline ADI-R scores, S score = ADI-R scores on day 3 of the challenge test administration.

We report a significant worsening of ADI-R subscales ADI-SI, ADI-C and ADI-RI in all 5 patients following broccoli sprout extract (sulforaphane) administration in the context of a challenge test. Experienced clinician and parental/primary caretaker reported observation served to determine CGI-I score after 3 days of broccoli sprout extract (sulforaphane) administration.

TABLE 5

CGI-S and CGI-I values after challenge test

| Patient | GGI-S | CGI-I | Clinical significance |
|---|---|---|---|
| Patient 1 | 5 | 6 | Much worse |
| Patient 2 | 6 | 6 | Much worse |
| Patient 3 | 6 | 7 | Very much worse |
| Patient 4 | 5 | 7 | Very much worse |
| Patient 5 | 4 | 6 | Much worse |

The invention claimed is:

1. A method of treating an autism spectrum disorder (ASD) in a patient, comprising administering a therapeutically effective amount of an Nrf2-inhibitor, which is not ascorbic acid or luteolin, to a patient who has been determined to be suffering from ASD phenotype 1, wherein whether the patient suffers from ASD phenotype 1 has been determined by administering the patient an Nrf2-activator and identifying the patient as suffering from ASD phenotype 1 if the patient shows a negative response.

2. The method according to claim 1, wherein the Nrf2-inhibitor is selected from the group consisting of Kelch-like ECH-associated protein 1, cytosolic inhibitor of Nrf2, INRF2, Kelch-like protein 19, KIAA0132, KLHL19, Kelch-like ECH-associated protein 1 zebrafish, Maft protein zebrafish, Keap 1 protein rat, trigonelline (N-methylnicotinate), tamibarotene, all-trans retinoic acid (ATRA), 4-methoxychalcone, 3',4',5',5,7-Pentamethox-yflavone (PMF), Epigalocatechin 3-gal-late (EGCG), isoniazid (INH), ethionamide (ETH), ARE expression modulator (AEM1), brusatol (Bru), cryptoanshinone (CryP), IM3829 (4-(2- cyclohexylethoxy)aniline), metformin (Met), mycotoxin ochratoxin A (Ota), triptolide (TPL), thiuram disulfides and disulfiram.

* * * * *